United States Patent
Sohège et al.

[19]

[11] Patent Number: 6,075,444
[45] Date of Patent: Jun. 13, 2000

[54] ARRANGEMENT FOR BLOCKING THE OPERATION BY AN OPERATOR OF A VEHICLE OR A MACHINE

[75] Inventors: Jürgen Sohège, Stockelsdorf; Hans Matthiessen, Bad Schwartau, both of Germany

[73] Assignee: Dräger Sicherheitstechnik GmbH, Lübeck, Germany

[21] Appl. No.: 09/149,083

[22] Filed: Sep. 8, 1998

[30] Foreign Application Priority Data

Sep. 25, 1997 [DE] Germany ............... 197 42 261

[51] Int. Cl.$^7$ ................................ G08B 23/00
[52] U.S. Cl. ............ 340/576; 340/426; 340/539; 180/272
[58] Field of Search ............... 340/576, 439, 340/425.5, 426, 539; 307/10.2, 10.3; 180/272, 275

[56] References Cited

U.S. PATENT DOCUMENTS

| | | | |
|---|---|---|---|
| 4,592,443 | 6/1986 | Simon | 180/272 |
| 4,613,845 | 9/1986 | Du Bois | 340/576 |
| 4,689,603 | 8/1987 | Conigliaro et al. | 340/576 |
| 4,809,810 | 3/1989 | Elfman et al. | 180/272 |
| 4,912,458 | 3/1990 | Comeau et al. | 340/576 |
| 4,926,164 | 5/1990 | Porter et al. | 340/576 |
| 5,220,919 | 6/1993 | Phillips et al. | 128/632 |
| 5,396,215 | 3/1995 | Hinkle | 340/426 |
| 5,426,415 | 6/1995 | Prachar et al. | 340/576 |

FOREIGN PATENT DOCUMENTS

WO 94/07407  4/1994  WIPO .

*Primary Examiner*—Daniel J. Wu
*Assistant Examiner*—Van T. Trieu
*Attorney, Agent, or Firm*—Walter Ottesen

[57] ABSTRACT

The invention is directed to an arrangement for blocking the operation by an intoxicated operator of a machine or a motor vehicle. The arrangement has a measuring apparatus which determines the blood alcohol content of the operator and an evaluation unit connected to the machine or motor vehicle. The evaluation unit receives measurement data supplied by the measurement apparatus and enables the machine or motor vehicle when the measurement data satisfies at least one predetermined condition. The arrangement is improved in that the sobriety of the operator is recognized before the starting operation of the machine or motor vehicle without it being necessary to supply a breath sample. The measuring apparatus includes a gas sensor which is a sensor for measuring the blood alcohol content via permeation through the skin of the operator. The measuring apparatus is configured so that it can be worn by the operator preferably on the leg or arm.

12 Claims, 1 Drawing Sheet

ARRANGEMENT FOR BLOCKING THE OPERATION BY AN OPERATOR OF A VEHICLE OR A MACHINE

BACKGROUND OF THE INVENTION

An arrangement for blocking the operation by an operator of machinery is disclosed in U.S. Pat. No. 4,613,845. The arrangement prevents a driver, who is intoxicated, from starting a motor vehicle. For this purpose, an alcohol sensor and a distance sensor are mounted on the steering wheel of the vehicle and are connected via an evaluating unit to on-board electronics of the motor vehicle. The distance sensor recognizes the operational readiness of the alcohol sensor and ensures that the alcohol sensor is not covered by a foil. Starting the vehicle is prevented if the alcohol sensor supplies a measured value which indicates a significant breath alcohol content.

Alcohol measuring devices are known which measure the alcohol content in a person through the skin and which permit a continuous wear thereof by means of a belt which is applied about the arm or the leg. In this way, measured values are available which continuously show the alcohol concentration. The measured data is transmitted to a central station by a data line. Such a measuring device is disclosed in international patent publication WO 94/07407 (PCT/US 92/08196).

U.S. Pat. No. 4,912,458 discloses a so-called sobriety interlock system wherein the driver must blow a breath sample into a measuring device before starting the vehicle which then evaluates the breath sample with respect to alcohol content and the manner in which the breath sample is supplied. It is disadvantageous in such an arrangement that another person can observe that the driver has outputted a breath alcohol sample for starting the vehicle.

SUMMARY OF THE INVENTION

It is an object of the invention to provide an arrangement which prevents an inebriated person from starting a vehicle or a machine. It is a further object of the invention to detect the sobriety of the operator in advance of the starting operation without the necessity of supplying a breath sample.

The arrangement of the invention is for blocking the operation by an intoxicated operator of a machine including a motor vehicle. The arrangement includes: a measuring apparatus for determining the blood alcohol content of the operator; the measuring apparatus including attachment means for attaching the measuring apparatus to a body portion of the operator; the measuring apparatus also including a gas sensor mounted therein and the gas sensor being a sensor measuring the blood alcohol content via permeation through the skin of the operator; an evaluation unit operatively connected to the machine and having an output for emitting an enable signal to the machine to permit the operator to operate the same; an interface between the measuring apparatus and the evaluation unit for passing a signal representing measurement data indicative of the blood alcohol content from the measuring apparatus to the evaluation unit; and, the evaluation unit including means for evaluating the measurement data and for outputting the enable signal via the output when the measurement data satisfies at least one predetermined condition.

The advantage of the invention is that a continuous control of the blood alcohol content is made possible during operation of the vehicle. This is achieved by the application of a transcutaneous alcohol measuring device to a part of the body of a person to be monitored and by transmitting the measured values to an arrangement with which the operation of the vehicle or machine can be enabled. The measuring device can be worn covered on the body, for example, on the leg of the person where it is covered by the trousers. It is also purposeful to apply the measuring device to the right lower arm.

A wireless transmitting path is provided in an advantageous manner between the measuring device and the evaluation unit. For this purpose, transmission systems are suitable which operate optically, magnetically or at high frequency. It is also purposeful to configure the transmission path so that it is bi-directional. In this way, a data communication between the measuring device and the evaluation unit is possible.

A memory for storing an identifier specific to the user is provided in the measuring device and the evaluation unit is so configured that this identifier can be read out of the measuring device in order to identify the identifier so that only measurement data of a designated operator can be processed by the evaluation unit.

A timer is provided in the evaluation unit which is activated after the operation is enabled for the first time and, according to a pregiven time pattern, a control signal is outputted to the evaluation unit by which a renewed evaluation of measured data is started. The time pattern can be permanently pregiven or the time pattern can be generated by a random generator so that the person monitored does not know when the next measurement evaluation is executed.

It is advantageous to additionally connect a breath alcohol measuring device to the evaluation unit so that the vehicle can be started by a person which is not equipped with a transcutaneous measuring alcohol measuring device.

BRIEF DESCRIPTION OF THE DRAWINGS

The invention will now be described with reference to the single figure (FIG. 1) of the drawing which shows a transcutaneous alcohol measuring device and an evaluation unit mounted in a vehicle.

DESCRIPTION OF THE PREFERRED EMBODIMENTS OF THE INVENTION

Figure 1:
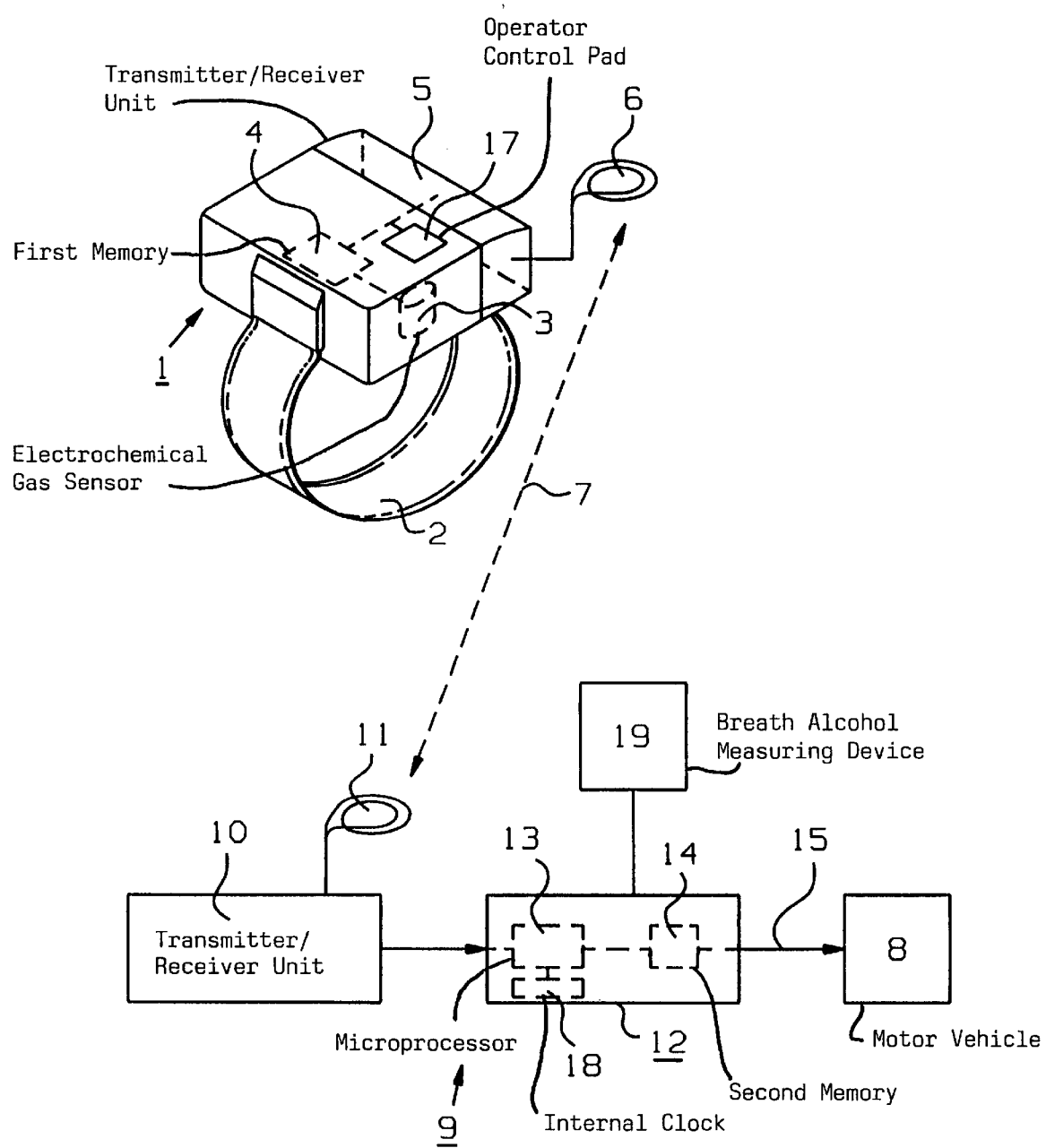

A measuring device 1 is attached with a belt 2 to the leg of a person (not shown) whose blood alcohol concentration is to be monitored. For this purpose, the measuring device 1 includes an electrochemical gas sensor 3 which lies against the surface of the skin of the person and detects the blood alcohol content via permeation through the skin. The measured blood alcohol concentration values are stored in a first memory 4. The measuring device 1 further includes a first transmitter/receiver unit 5 having a first magnetic contact loop 6. The blood alcohol concentration values determined by the measuring device 1 are transmitted from the first transmitter/receiver unit 5 and the first magnetic contact loop 6 along a transmission path 7 to an evaluation unit 9 connected to a vehicle 8.

The evaluation unit 9 essentially comprises a second transmission/receiving unit 10 having a second magnetic contact loop 11 and an arithmetic unit 12 having a microprocessor 13 and a second memory 14. The evaluation unit 9 is connected to the electric ignition unit of the vehicle 8 in such a manner that the vehicle 8 can be started only after the output of an enabling signal.

The operation of the arrangement of the invention will now be described.

A few minutes before the vehicle 8 is taken into service, the measuring device 1 is attached with the belt 2 to the leg of the person to be monitored. To identify the person, a user-specific identifier is read into the first memory 4 of the measuring device 1 via an operator control pad 17 so that the alcohol concentration measurement values, which are detected by the electrochemical gas sensor 3, can be directly assigned to the monitored person. After the measuring device 1 is placed, the transcutaneous measurement of the alcohol concentration is started via the operator control pad 17. The measuring device 1 contains in addition a distance sensor (not shown in FIG. 1), which monitors that the measuring device 1 is not removed after the start of the measurement.

The communication between the measuring device 1 and the evaluation unit 9 takes place via the magnetic contact loops (6, 11). The first magnetic contact loop 6 is an integral component of the measuring device 1 and is shown as a separate component only to improve clarity in the drawing. The second magnetic contact loop 11 is mounted in the foot area of the vehicle 8 in close proximity to the measuring device 1 so that the transmission path 7 is limited to the smallest possible distance path.

The data transmission along the transmission path 7 takes place bi-directionally via the transmitter/receiver units (5, 10) between the first memory 4 of the measuring device 1 and the microprocessor 13 and the second memory 14 of the evaluation unit 9.

Before starting the vehicle 8, the evaluation unit 9 is activated by the person to be monitored in that the person indicates that he or she wants to start the vehicle. This is done when the person inserts an ignition key (not shown). The microprocessor 13 then reads out the following from the first memory 4 via the transmitter/receiver units (5, 10): the alcohol concentration measured values measured by the electrochemical gas sensor 3, the time point of the start of the measurements and the identifier specific to the user. These data are first stored in the second memory 14 of the arithmetic unit 4. To verify the read-in data, the second memory contains a list having authorized user-specific identifiers in order to ensure that the vehicle can only be started by specific persons. A comparison of the identifier of the measuring device 1 to the identifiers stored in the second memory 14 is carried out in the microprocessor 13. Furthermore, the alcohol concentration measurement values, which were measured by the gas sensor 3, are compared to the limit values stored in the second memory 14. An enabling signal is transmitted via line 15 to the on-board electronics of the vehicle 8 provided that the user identifiers are coincident and the measured alcohol concentration measurement values lie below the limit values and that the measuring device 1 was applied a specific time span in advance of the start operation. The start of the vehicle 8 is possible with the enabling signal.

An internal clock 18 is provided within the arithmetic unit 12 and is activated after the output of the enabling signal. According to a pregiven or random time pattern, control signals are outputted by the internal clock 18 to the microprocessor 13. These control signals initiate a renewed evaluation of the alcohol concentration measurement values by the evaluation unit 9. The time span for one of the following measurements can then be between approximately five minutes and an hour. If the microprocessor 13 determines that the limit values were exceeded in the subsequent evaluations of the measured alcohol concentration measurement values, the driver, depending upon the extent to which the limit values are exceeded, receives either a message that he must stop for several minutes or he can continue to drive but the illumination devices (not shown) of the vehicle 8 begin to blink periodically.

In another embodiment of the invention, an additional breath alcohol measuring device 19 can be connected in order to permit another person, who is not equipped with the measuring device 1, to start the vehicle 8.

It is understood that the foregoing description is that of the preferred embodiments of the invention and that various changes and modifications may be made thereto without departing from the spirit and scope of the invention as defined in the appended claims.

What is claimed is:

1. An arrangement for blocking an intoxicated operator from operating a motor vehicle having an electric ignition, the intoxicated operator having a blood alcohol content and the arrangement comprising:

a measuring apparatus for determining the blood alcohol content of the operator;

said measuring apparatus including a strap for attaching said measuring apparatus to a limb of said operator;

said measuring apparatus also including a gas sensor mounted therein and said gas sensor being disposed so as to lie against the surface of the skin of said operator to measure said blood alcohol content via permeation through the skin;

an evaluation unit physically separate from said measuring apparatus and operatively connected to said motor vehicle and having an output for emitting an enable signal to said motor vehicle to permit said operator to start and operate said motor vehicle;

an interface between said measuring apparatus and said evaluation unit for passing a signal representing measurement data indicative of said blood alcohol content from said measuring apparatus to said evaluation unit;

said interface being a wireless, bidirectional transmission path between said measuring apparatus and said evaluation unit;

said evaluation unit including means for evaluating said measurement data and for outputting said enable signal via said output when said measurement data satisfies at least one predetermined condition;

said measuring apparatus including a memory for storing an identifier specific to said operator; and, said evaluation unit including: means for detecting said identifier;

means for comparing said measured data to said predetermined condition only after detection and identification of said identifier; and, said output of said evaluation unit being connected to said electric ignition of said motor vehicle so that said motor vehicle can be started only after said enable signal is outputted.

2. The arrangement of claim 1, said evaluation unit further including an internal clock which is activated after said enable signal is outputted and said internal clock functioning to output a signal within said evaluation unit in accordance with a pregiven time pattern for triggering a renewed comparison of said measurement data then present to said at least one predetermined condition so as to permit a continuous control of the blood alcohol content of said operator during the operation of said vehicle.

3. The arrangement of claim 1, further comprising a breath alcohol measuring device connected to said evaluation unit so that said vehicle can be started and operated by a person not equipped with said measuring device for measuring alcohol blood content via permeation through the skin.

4. An arrangement for blocking an intoxicated operator from operating a motor vehicle, the intoxicated operator having a blood alcohol content and the arrangement comprising:

a measuring apparatus for determining the blood alcohol content of the operator;

said measuring apparatus including attachment means for attaching said measuring apparatus to a body portion of said operator;

said measuring apparatus also including a gas sensor mounted therein and said gas sensor being a sensor measuring said blood alcohol content via permeation through the skin of said operator;

an evaluation unit operatively connected to said vehicle and having an output for emitting an enable signal to said vehicle to permit said operator to operate said vehicle;

a wireless transmission path between said measuring apparatus and said evaluation unit for passing a signal representing measurement data indicative of said blood alcohol content from said measuring apparatus to said evaluation unit;

said evaluation unit including means for evaluating said measurement data and for outputting said enable signal via said output when said measurement data satisfies at least one predetermined condition;

said evaluation unit further including an internal clock which is activated after said enable signal is outputted and said internal clock functioning to output a signal within said evaluation unit in accordance with a pre-given time pattern during the operation of said motor vehicle for triggering a renewed comparison of said measurement data then present to said at least one predetermined condition so that a continuous control of said alcohol blood content is made during said operation of said motor vehicle; and, a breath alcohol measuring device connected to said evaluation unit so that said vehicle can be started and operated by a person not equipped with said measuring apparatus for measuring alcohol blood content via permeation through the skin.

5. The arrangement of claim 4, said attachment means comprising a strap for attaching said apparatus to a limb of said operator.

6. The arrangement of claim 4, wherein said wireless transmission path is a bidirectional transmission path.

7. The arrangement of claim 4, said measuring apparatus including a first memory for storing an identifier specific to said operator; and, said evaluation unit including: means for detecting said identifier; and, means for comparing said measured data to said predetermined condition only after detection and identification of said identifier.

8. An arrangement for blocking an intoxicated operator from operating a motor vehicle, the intoxicated operator having a blood alcohol content and the arrangement comprising:

a measuring apparatus for determining the blood alcohol content of the operator;

said measuring apparatus including attachment means for attaching said measuring apparatus to a body portion of said operator;

said measuring apparatus also including a gas sensor mounted therein and said gas sensor being a sensor measuring said blood alcohol content via permeation through the skin of said operator;

an evaluation unit mounted on said vehicle and being physically separated from said measuring apparatus;

said evaluation unit being operatively connected to said vehicle and having an output for emitting an enable signal to said vehicle to permit said operator to operate said vehicle;

a wireless interface between said measuring apparatus and said evaluation unit for passing a signal representing measurement data indicative of said blood alcohol content from said measuring apparatus to said evaluation unit;

said evaluation unit further including an internal clock which is activated after said enable signal is outputted and said internal clock functioning to output a signal within said evaluation unit in accordance with a random time pattern during the operation of said motor vehicle for triggering a renewed comparison of said measurement data then present to said at least one predetermined condition so that said operator cannot know when the next measurement evaluation is made and so that a continuous control of said alcohol blood content is made during said operation of said motor vehicle;

said evaluation unit including means for evaluating said measurement data and for outputting said enable signal via said output when said measurement data satisfies at least one predetermined condition.

9. The arrangement of claim 8, said attachment means comprising a strap for attaching said apparatus to a limb of said operator.

10. The arrangement of claim 8, wherein said transmission path is a bidirectional transmission path.

11. The arrangement of claim 10, said measuring apparatus including a first memory for storing an identifier specific to said operator; said evaluation unit including: means for detecting said identifier; and, means for comparing said measured data to said predetermined condition only after detection and identification of said identifier.

12. The arrangement of claim 8, further comprising a breath alcohol measuring device connected to said evaluation unit so that said vehicle can be started and operated by a person not equipped with a measuring device for measuring alcohol blood content via permeation through the skin.

* * * * *